United States Patent [19]

Smith et al.

[11] 4,309,443

[45] Jan. 5, 1982

[54] CINNAMIC ACID DERIVATIVES, THEIR PREPARATION, AND PHARMACEUTICAL COMPOSITIONS CONTAINING THEM

[75] Inventors: David G. Smith, Redhill; Anthony T. Ainsworth, Cranleigh, both of England

[73] Assignee: Beecham Group Limited, England

[21] Appl. No.: 183,715

[22] Filed: Sep. 3, 1980

[30] Foreign Application Priority Data

Sep. 6, 1979 [GB] United Kingdom .............. 31006/79
May 16, 1980 [GB] United Kingdom .............. 16348/80

[51] Int. Cl.³ .................. A61K 31/195; C07C 101/30; C07C 103/26; A61K 31/165
[52] U.S. Cl. .................. 424/319; 260/501.11; 260/501.12; 560/21; 560/42; 560/34; 560/12; 560/13; 562/451; 562/430; 562/435; 562/439; 564/49; 564/51; 564/99; 564/162; 564/165; 424/309; 424/316; 424/321; 424/322; 424/324
[58] Field of Search .............. 562/451, 430, 435, 439; 560/42, 21, 34, 12, 13; 564/165, 49, 51, 99, 162; 424/309, 319, 316, 321, 322, 324; 260/501.11, 501.12

[56] References Cited

U.S. PATENT DOCUMENTS

| | | |
|---|---|---|
| 3,818,101 | 6/1974 | Baile et al. |
| 3,828,095 | 8/1974 | Boschetti et al. .............. 564/165 |
| 3,836,666 | 9/1974 | Koppe et al. .............. 424/319 |
| 3,857,873 | 12/1974 | Schwender et al. .............. 424/319 |
| 3,872,147 | 3/1975 | Koppe et al. .............. 424/319 |
| 4,146,638 | 3/1979 | Renth et al. .............. 560/42 |
| 4,165,384 | 8/1979 | Carlsson et al. .............. 564/165 |
| 4,191,765 | 3/1980 | Fritsch et al. .............. 562/451 |

FOREIGN PATENT DOCUMENTS 31763 2/1968 South Africa .

OTHER PUBLICATIONS

Hartley et al., J. Med. Chem., vol. 13, No. 4 (1970), pp. 674–680.

Primary Examiner—G. T. Breitenstein
Attorney, Agent, or Firm—Jacobs & Jacobs

[57] ABSTRACT

A compound of the formula (I):

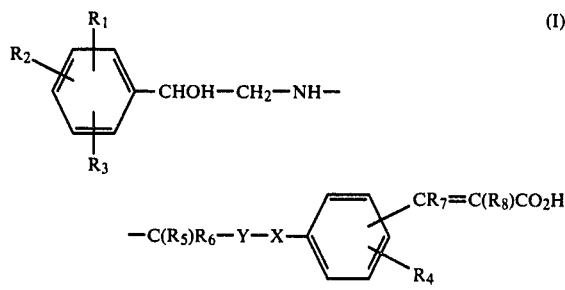

or a pharmaceutically acceptable ester, amide or salt thereof wherein $R_1$ is a hydrogen, fluorine, chlorine or bromine atom or a hydroxyl, hydroxymethyl, methyl, methoxyl, amino, formamido, acetamido, methylsulphonylamido, nitro, benzyloxy, methylsulphonylmethyl, ureido, trifluoromethyl or p-methoxybenzylamino group; $R_2$ is a hydrogen, fluorine, chlorine or bromine atom or a hydroxyl group; $R_3$ is a hydrogen, chlorine or bromine atom or a hydroxyl group; $R_4$ is a hydrogen, chlorine or fluorine atom or a methyl, methoxyl or hydroxyl group or a carboxylic acid group or a salt, ester or amide thereof; $R_5$ is a hydrogen atom or a methyl group; $R_6$ is a hydrogen atom or a methyl group; $R_7$ is a hydrogen atom or a methyl or ethyl group; $R_8$ is a hydrogen atom or a methyl or ethyl group; X is an oxygen atom or a bond, and Y is an alkylene group of up to 5 carbon atoms, or a bond has been found to possess anti-obesity and/or anti-hyperglycaemic activity.

17 Claims, No Drawings

CINNAMIC ACID DERIVATIVES, THEIR PREPARATION, AND PHARMACEUTICAL COMPOSITIONS CONTAINING THEM

The present invention relates to a group of secondary amine derivatives that possess anti-obesity and anti-hyperglycaemic properties, to the method of their preparation and to their use as anti-obesity and/or anti-hyperglycaemic agents when formulated into a pharmaceutical composition.

Certain of the compounds within the formula (I):

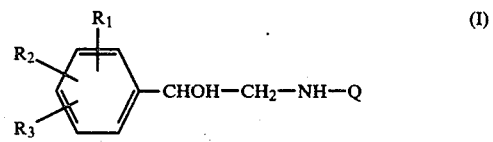

wherein $R_1$ is a hydrogen, fluorine or chlorine atom or a hydroxyl, hydroxymethyl, methyl, methoxyl, amino, formamido, acetamido, methylsulphonylamido, nitro, benzyloxy, methylsulphonylmethyl, ureido, trifluoromethyl or p-methoxybenzylamino group; $R_2$ is a hydrogen, fluorine or chlorine atom or a hydroxyl group; $R_3$ is a hydrogen or chlorine atom or a hydroxyl group; and Q is an isopropyl or t-butyl group; are known to possess β-adrenoceptor agonist activity (see for example D. T. Collins et al, J. Med. Chem., 1970, 13, 674). Certain compounds within formula (I) wherein Q is a group such as a phenylaminoethyl were disclosed in Belgian Pat. No. 851232 as possessing β-adrenoceptor stimulant activity. Belgian Pat. No. 809831 disclosed that certain compounds within formula (I) wherein Q is inter alia a substituted phenylethyl group are useful as medicaments for the treatment of skin diseases. U.S. Pat. No. 3,818,101 disclosed certain compounds within formula (I) wherein Q could be inter alia an aralkyl group which may be used to induce polyphagia in meat producing animals. Certain compounds within the formula (I) wherein Q may be hydroxybenzyl or alkoxybenzyl group were indicated as possessing β-adrenergic stimulant and blocking properties in South African Patent No. 67/5591. The preceding publications do not describe compounds of the formula (I) as possessing anti-obesity activity coupled with anti-hyperglycaemic activity nor indeed do they describe compounds of the formula (I) as possessing anti-obesity activity alone. We have discovered a group of compounds somewhat related to those of the formula (I) which possess anti-obesity properties and/or anti-hyperglycaemic properties. Such compounds may thus be used in the treatment of obesity or hyperglycaemia and can be envisaged as being of particular interest in conditions such as maturity onset diabetes where obesity is often linked with hyperglycaemia.

The present invention provides the compounds of the formula (II):

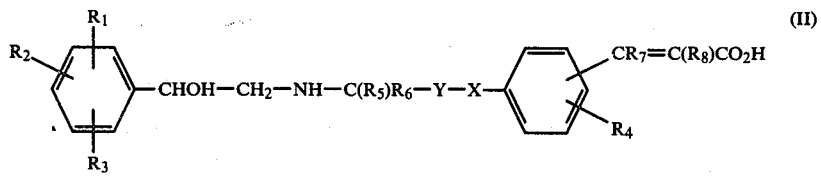

or a pharmaceutically acceptable ester, amine or salt thereof wherein $R_1$, $R_2$ and $R_3$ are as defined in relation to formula (I) or are each independently a bromine atom; $R_4$ is a hydrogen, chlorine or fluorine atom or a methyl, methoxyl or hydroxyl group or a carboxylic acid group or a salt, ester or amide thereof; $R_5$ is a hydrogen atom or a methyl group; $R_6$ is a hydrogen atom or a methyl group; $R_7$ is a hydrogen atom or a methyl or ethyl group; $R_8$ is a hydrogen atom or a methyl or ethyl group; X is an oxygen atom or a bond; and Y is an alkylene group of up to 5 carbon atoms or a bond.

Preferred compounds are $C_{1-6}$ alkyl esters of the compounds of formula (II), suitably the methyl or ethyl esters.

Other preferred compounds according to the invention are amides of formula (III):

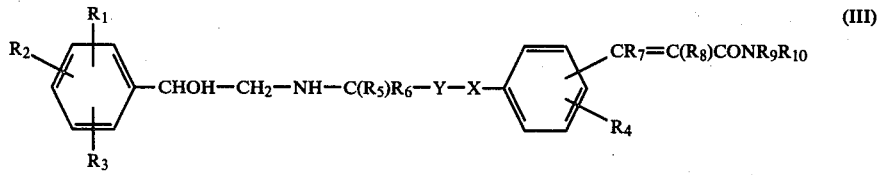

in which $R_1$ to $R_8$, X and Y are as defined in formula (II) and $R_9$ and $R_{10}$ are each a $C_{1-4}$ alkyl group, preferably methyl, or a hydrogen atom.

Most suitably the —$CR_7$= group is attached para- to the X moiety.

Apt values for $R_1$ include the hydrogen, fluorine, chlorine and bromine atoms and the hydroxymethyl, hydroxyl, trifluoromethyl, methoxyl, acetamido, amino, methylsulphonylmethyl, methylsulphonamido, ureido or p-methoxybenzylamino group.

Suitably X in the compounds of the formula (II) is an oxygen atom but more suitably X in the compounds of the formula (II) is a bond.

The moiety Y may be branched if desired, for example in such a manner that it carried one or two methyl groups. However it is more convenient that Y is unbranched. Favoured groups Y are of the formula —$(CH_2)_n$— where n is an integer from 1 to 5.

A particularly suitable value for $R_2$ is the hydrogen atom.

Aptly $R_3$ is a hydrogen atom. Aptly $R_3$ is a hydroxyl group.

Particularly suitable groups $R_1R_2R_3C_6H_2$ include the phenyl, 3-chlorophenyl, 4-chlorophenyl, 3-trifluoromethylphenyl, 2-fluorophenyl, 3-fluorophenyl, 2-chlorophenyl and 3-bromophenyl groups.

A preferred group $R_1R_2R_3C_6H_2$ is the phenyl group. Another preferred group $R_1R_2R_3C_6H_2$ is the 3-chlorophenyl group, and another is the 3-trifluoromethyl group.

A favourable value for $R_5$ is a hydrogen atom. A further favourable value for $R_5$ is the methyl group. A favourable value for $R_6$ is the hydrogen atom. A further favourable value for $R_6$ is the methyl group. Most favourably $C(R_5)R_6$ is a $CH_2$, $CHCH_3$, or $C(CH_3)_2$ group. The compounds of this invention wherein $C(R_5)R_6$ is a $CH_2$ or $C(CH_3)_2$ group tend to be less potent as anti-obesity agents than those wherein $C(R_5)R_6$ is a $CH(CH_3)$ group but since they possess one less centre of asymmetry they offer the advantage of a slightly easier synthesis. The compounds wherein $C(R_5)R_6$ is a $CH(CH_3)$ group offer the considerable advantage of higher potency as anti-obesity agents.

In the compounds of the invention wherein Y is —$(CH_2)_n$— group it is most suitable that n is 1,2,3 or 4. Particularly suitable values for n are 1, 2 and 3.

A favoured value for $R_7$ is the hydrogen atom or methyl group. A preferred value for $R_8$ is the hydrogen atom or methyl group.

One group of preferred compounds of this invention are those of the formula (IV):

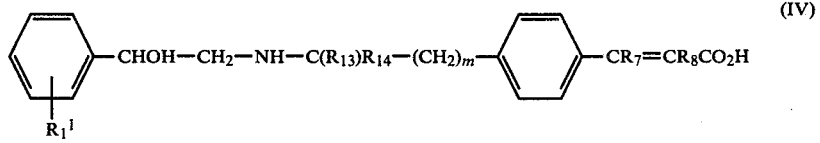

or a pharmaceutically acceptable salt or ester thereof wherein $R_{13}$ is a hydrogen atom or a methyl group; $R_{14}$ is a hydrogen atom or a methyl group; m is 1, 2 or 3 and $R_1^1$ is a hydrogen, chlorine, fluorine or bromine atom, or a trifluoromethyl group, $R_7$ is a hydrogen atom or a methyl group, and $R_8$ is a hydrogen atom or a methyl group.

Another group of preferred compounds of this invention are those of the formula (V):

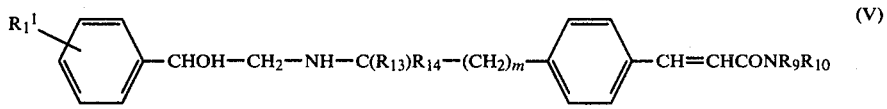

or a pharmaceutically acceptable salt thereof, in which $R_1^1$, $R_{13}$, $R_{14}$ and m are defined with respect to formula (IV) and $R_9$ and $R_{10}$ are defined with respect to formula (III).

Preferably the $R_1^1C_6H_5$ group is 3-chlorophenyl, 3-fluorophenyl, 2-fluorophenyl, 3-trifluoromethylphenyl, 3-bromophenyl or phenyl.

Most suitably $R_{13}$ is a hydrogen atom. Most suitably $R_{14}$ is a methyl group. Favourably m is 1. Favourably m is 2.

The compounds of this invention may be provided as acid addition salts. Such salts may be of an organic or inorganic acid but are normally salts with a pharmaceutically acceptable acid. Suitable acid addition salts include those formed with acids such as hydrochloric, hydrobromic, orthophosphoric, sulphuric, methanesulphonic, toluenesulphonic, acetic, propionic, lactic, citric, fumaric, malic, succinic, salicylic, acetylsalicylic or the like acid.

The compounds of the formula (II) have a centre of asymmetry at the carbon atom marked with a single asterisk in formula (IIa):

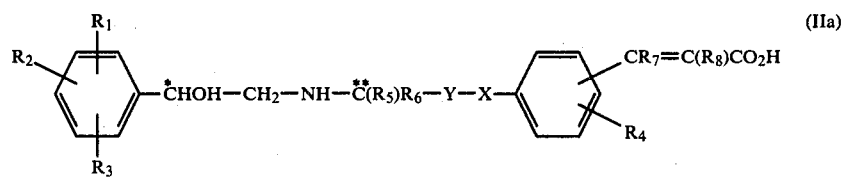

wherein $R_1$–$R_8$, Y and X are as defined in relation to formula (II). The compounds of the formula (II) have another centre of asymmetry at the carbon atom marked with two asterisks in formula (IIa) when $R_1$–$R_8$, Y and X are as defined in relation to formula (II) when $R_5$ is different from $R_6$.

The present invention extends to the individual stereoisomeric forms of the compounds of the formula (II) as well as to mixtures thereof. Aptly those compounds of the formula (II) which contain two asymmetric centres are provided in the form of the separated diastereoisomers. Such separated diastereoisomers will of course contain a pair of compounds which are mirror images of each other.

X-Ray analysis may be used to determine and correlate absolute stereochemistry.

It has been observed that in the $^{13}C$ NMR spectrum of a compound containing a methyl group on the carbon atom $\alpha$ to the nitrogenn atom (ie one existing in diastereoisomeric forms), the R*, R**; S*, S** diastereoisomer is that in which the methyl group appears at higher field (lower numerical value when expressed in ppm, typically <20 ppm downfield from tetramethylsilane) in $d_6$DMSO solution, whilst the lower field (higher numerical value, typically $\geq$20 ppm downfield from TMS) resonance is attributable to the R*, S**; S*, R** modification. The amount of each diastereoisomer may be estimated from the relative intensities of the absorption lines and is expressed in the examples as a ratio (R* R**, S* S**:R* S**, S* R**). Other paired resonances can occur for the carbon atoms attached directly to the nitrogen atom and the carbon β to nitrogen which carries the hydroxyl group.

The diastereoisomer ratio of said compounds may also be determined by the following gc technique.

To 250 μl of a solution of t-butyldimethylsilyl chloride (0.083 g) and imidazole (0.038 g) dissolved in pyridine (1 ml) was added the compound (~0.001 g) and the solution heated 1 h at 135° C. To this silylated mixture was added trifluoroacetylimidazole (25 μl) and the whole further heated for 0.5 h at 135° C.

0.2 μl of this solution was injected onto a 25 m SP-1000 W.C.O.T. capillary column contained in a Carlo Erba 4160 Gas Chromatograph under the following conditions.

Temperature of Injection block: 250°
Oven Temperature: 240°
Carrier Gas—Hydrogen at 2 ml/min through column
Split Ratio: 10:1

The diastereoisomers elute after about 25 mins and the ratio is determined by area integration using the spectrophysics SP-4000 data system.

The $-CR_7=CR_8CO_2H$ or $-CR_7=C-R_8-CONR_9R_{10}$ moiety of the hereinbefore described compounds may be cis but is more aptly trans.

The present invention also provides a pharmaceutical composition which comprises a compound of this invention and a pharmaceutically acceptable carrier.

The compositions of this invention will normally be formulated for oral administration although composition formulated for non-oral modes of administration, for example, injection, are also envisaged.

Particularly suitable oral dosage forms are unit dose forms such as tablets or capsules. Other fixed unit dose forms such as powders presented in sachets may also be used.

In accordance with conventional pharmaceutical practice the carrier may comprise a diluent, binder, filler, disintegrant, wetting agent, lubricant, colourant, flavourant or the like.

Typical carriers may therefore comprise such agents as microcrystalline cellulose, starch, sodium starch glycollate, polyvinylpyrrolidone, polyvinylpolypyrrolidone, magnesium stearate, sodium lauryl sulphate, sucrose and the like.

Most suitably the composition will be provided in unit dose form. Such unit doses will normally comprise 0.01 to 100 mg, more usually 0.2 to 50 mg and favourably 0.5 to 20 mg. Such doses may be taken one to six times a day in a manner such that the total daily dose for a 70 kg adult will generally be about 0.1 to 100 mg and more usually about 2 to 80 mg. The more potent preferred compounds will generally be in unit doses containing 0.1 to 10 mg and more usually 0.25 to 5 mg. Their daily dose will generally be about 0.5 to 20 mg, more usually 1 to 10 mg, for example 2 to 5 mg.

In addition to use in human medicine the compositions of this invention may be used to treat obesity in domestic mammals such as dogs. In general administration to domestic mammals may be by mouth and will usually take place one or two times a day at about 0.025 mg/kg to 2.5 mg/kg, for example 0.1 mg/kg to 2 mg/kg.

The present invention also provides a process for the preparation of a compound of this invention which comprises the reduction of a compound of the formula (VI):

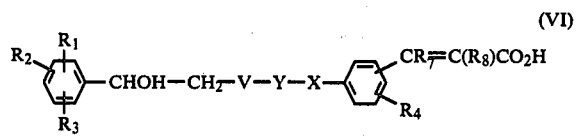

or its ester or amide wherein V is a $-N=CR_5$ or $-NH-CH(OH)R_5-$ group and $R_1$, $R_2$, $R_3$, $R_4$, $R_7$, $R_8$, Y and X are as defined in relation to formula (II) and thereafter if desired forming an addition salt of the initially produced compound of the formula (II).

The reduction of the compound of the formula (VI) may be effected using a complex hydride such as sodium borohydride or sodium cyanoborohydride.

This reduction is generally carried out in a lower alkanolic solvent, for example methanol.

An approximately ambient temperature may be employed, for example 20° to 30° C.

The desired compound may be obtained from the reaction mixture by evaporation, extraction into a suitable solvent such as ethyl acetate and evaporation. The initially obtained product may be purified conventionally, for example by chromatography or crystallisation or the like.

The compound of the formula (VI) may be prepared by the reaction of a compound of the formula (VII):

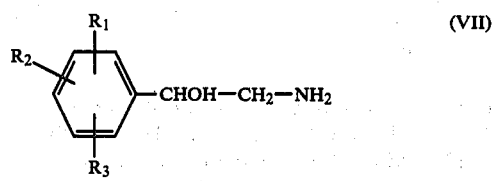

wherein $R_1$, $R_2$ and $R_3$ are as defined in relation to formula (II) with a compound of the formula (VIII):

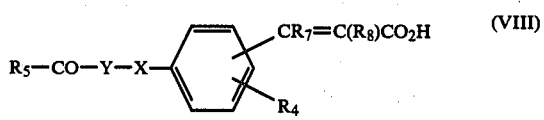

or its ester or amide wherein $R_4$, $R_5$, $R_7$, $R_8$, Y and X are as defined in relation to formula (II).

The condensation reaction may be performed in a conventional solvent such as a lower alkanol, for example ethanol or in benzene with azeotropic removal of water. In general the reaction is carried out at an elevated temperature, for example at the reflux temperature.

It is often convenient to prepare and utilize the compound of the formula (VI) in situ without isolation. In this case the reaction may comprise the reduction of a mixture of a compound of the formula (VII) and a compound of the formula (VIII) wherein $R_1$, $R_2$, $R_3$, $R_4$, $R_5$, $R_7$, $R_8$, X and Y are as defined in relation to formula (II).

Such a reduction may be carried out under conditions as described for the reduction of a compound of the formula (VI).

The compounds of the formula (II) as hereinbefore defined may also be prepared by the reaction of a compound of the formula (IX):

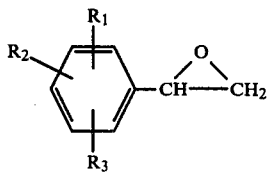

(IX)

wherein $R_1$, $R_2$ and $R_3$ are as defined in relation to formula (II) with a compound of formula (X):

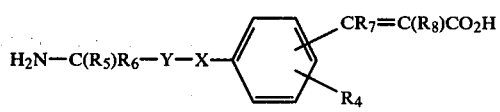

(X)

or its ester or amide wherein $R_4$, $R_5$, $R_6$, $R_7$, $R_8$, X and Y are as defined in relation to formula (II).

This reaction may be carried out in a lower alkanolic solvent such as methanol or ethanol.

A further method of preparing the compounds of the formula (II) comprises the reduction of a compound of the formula (XI):

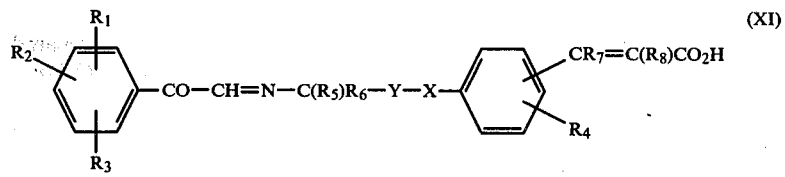

(XI)

or its ester or amide wherein $R_1$, $R_2$, $R_3$, $R_4$, $R_5$, $R_6$, $R_7$, $R_8$, X and Y are as defined in relation to formula (II).

The reduction of the compound of the formula (XI) may be carried out using a borohydride or the like as described for the reduction of the compound of the formula (VI)

The compound of the formula (XI) may be prepared by the reaction of a compound of the formula (XII)

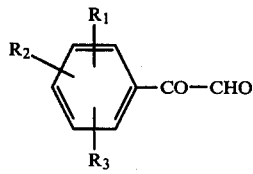

(XII)

or its hydrate or hemi-acetal of a lower alkanol wherein $R_1$, $R_2$ and $R_3$ are as defined in relation to formula (II), with a compound of the formula (X) as hereinbefore defined.

The preceding reaction is generally carried out under conditions that result in the removal of water formed during the reaction. Thus a convenient method is to azeotropically remove the water from a refluxing benzene solution using a Dean and Stark apparatus.

The compound of the formula (XI) may be obtained from the reaction mixture by evaporation of the solvent.

Compounds of the formula (II) containing only one centre of asymmetry may be resolved in known manner, for example using an optically active acid as a resolving agent. Compounds of the formula (II) containing two centres of asymmetry may be separated into their diastereoisomers by fractional crystallisation from a suitable solvent, for example from ethyl acetate. After such separation the individual components of the diastereoisomer may be obtained by resolution in known manner, for example using an optically active acid as a resolving agent.

Suitable optically active acids for use in resolution processes are described in Topics In Stereochemistry, Vol. 6, Wiley Interscience 1971, Allinger N.L. and Eliel W.L. eds.

Stereospecific synthesis may also be employed in order to obtain specific enantiomers. Thus, for example a single enantiomer of a compound of the formula (VII) may be used to react with a compound of the formula (VIII) prior to borohydride reduction. Similarly a single enantiomer of a compound of the formula (X) (where $R_5$ is not the same as $R_6$) may be used with a compound of the formula (IX). Similarly a single enantiomer of a compound of the formula (X) (where $R_5$ is not the same as $R_6$) may be used to react with a compound of the formula (XII) or prior to borohydride reduction. The specific enantiomers produced by these processes may then be separated by conventional means such as fractional crystallisation from a suitable solvent, for example ethyl acetate.

A further method of preparing the compounds of formula (III) comprises reacting a compound of formula (XIII):

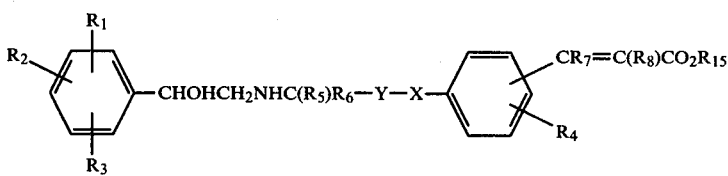

(XIII)

in which $R_1$–$R_8$, X and Y are as defined in relation to formula (II), and $R_{15}$ represents a $C_{1-4}$ alkyl group, with an amine of formula (XIV):

$R_9R_{10}NH$ (XIV)

wherein $R_9$ and $R_{10}$ are as defined in relation to formula (III).

The reaction is suitably carried out in the presence of an aqueous lower alkanolic solution, preferably aqueous methanol, at ambient temperature.

Preferably $R_{15}$ is methyl, $R_9$ is methyl and $R_{10}$ is a hydrogen atom.

The following Examples illustrate the invention; and the Descriptions illustrate the preparation of useful intermediates:

EXAMPLE 1

N-{2-(4-{(E)-2-Carbomethoxyethenyl}phenyl)-1-methylethyl}2-hydroxy-2-phenylethanamine A mixture of 4-(E)-(2-carbomethoxyethenyl)phenylpropan-2-one (2.18 g) and 2-hydroxy-2-phenylethanamine (1.37 g) was refluxed in benzene under a Dean and Stark apparatus until the theoretical amount of water had been collected. The solvent was evaporated, methanol added, and sodium borohydride (1.0 g) added portionwise at room temperature. The solution was left to stir for 0.5 h, and solvent removed. Water was added, the mixture extracted with ether and the combined ether layers dried ($MgSO_4$). Removal of the solvent gave the title compound, isolated as a 1:1 mixture of diastereoisomers, as the hemi-fumarate hemihydrate mp 99°–100.5° (ethyl acetate). $\tau$ (DMSO) 8.95 (3H, d, J=6 Hz), 6.4–7.5 (5H, m), 6.31 (3H, s), 5.2–4.9 (1H, m), 3.45 (1H, d, J=16 Hz+2H, s), 2.15–2.9 (10H, m), 1.6 (4H, s, disappears with $D_2O$).

EXAMPLE 2

N-{2-(4-{(E)-2-Carboxamidoethyl}phenyl)-1-methylethyl}-2-hydroxy-2-(3-chlorophenyl) ethanamine A mixture of 4-(E)-{(2-carboxamidoethenyl)phenylpropan-2-one (1.16 g) and 2-hydroxy-2-(3-chlorophenyl) ethanamine (0.98 g) was refluxed in benzene under a Dean and Stark apparatus until the theoretical volume of water had been collected (~4 h). The solvent was evaporated, methanol added and sodium borohydride (2.0 g) added portionwise. The solvent was evaporated, the residue partitioned between water and chloroform and the chloroform layer dried ($MgSO_4$). Removal of the solvent gave an oil which was chromatographed on Kieselgel 60. Elution with 10–15% methanol-chloroform gave the title compound as a 22:78 mixture of diastereoisomers, m.p. 170°–173° C. ($CHCl_3$). $\tau$ ($CDCl_3$). 9.05 (3H, d, J=6 Hz), 6.4–7.5 (9H, m), 5.5 (1H, m), 3.58 (1H, d, J=16 Hz), 2.24–3.0 (9H, m).

EXAMPLE 3

N-{2-(4{(E)-2-N'-Methylcarboxamidoethenyl}phenyl)-1-methylethyl}-2-hydroxy-2-(3-chlorophenyl) ethanamine This was prepared in an identical manner to the compound described in Example 2 replacing 4-(E)-(2-carboxamidoethenyl) phenylpropan-2-one by 4-(E)-(2-N'-methylcarboxamidoethenyl) phenylpropan-2-one. Chromatography of the resulting oil on Kieselgel 60 and elution with 5% methanol-chloroform gave the title compound as a 25:75 mixture of diastereoisomers, m.p. 98°–125° C. (EtOAc). $\tau$($CDCl_3$) 8.9 (3H, d, J=6 Hz), 7.48 (3H, d, J=4 Hz, collapses to a singlet with $D_2O$), 6.35–7.8 (6H, m; 1H disappears with $D_2O$), 5.45 (1H, t, J=5 Hz), 4–5 (1H, broad, disappears with $D_2O$), 3.45 (1H, d, J=16 Hz), 2.45–2.9 (9H, m), 2.01 (1H, q, J=4 Hz, disappears slowly with $D_2O$.)

EXAMPLE 4

N-{2-(4-{(E)-2-Carbomethoxyethenyl}phenyl)-1-methylethyl}-2-hydroxy-2-(4-chlorophenyl)ethanamine This was prepared in an identical manner to the compound described in Example 1 using 2-hydroxy-2-(4-chlorophenyl) ethanamine (1.97 g) and 4-}(E)-2-carbomethoxyethenyl} phenylpropan-2-one (2.55 g). The title compound was obtained as an oil (4.0 g) which was crystallized from hexane as a ~1:1 ratio of diastereoisomers (0.86 g) m.p. 76°–102° C. $\gamma$ ($CDCL_3$) 8.85 (3H, d, J=6 Hz), 6.9–7.6 (7H, m, 2H disappears with $D_2O$), 6.25 (3H, s), 5.45 (1H, m), 3.65 (1H, d, J=16 Hz), 2.9 (2H, d, J=8 Hz), 2.8 (4H, s), 2.6 (2H, d, J=8 Hz), 2.35 (1H, d, J=16 Hz).

EXAMPLE 5

N-{2-(4-{(E)-2-Carbomethoxyethenyl}phenyl)-1-methylethyl}-2-hydroxy-2-(3-chlorophenyl)ethanamine This was prepared in an identical manner to the compound described in Example 1 using 2-hydroxy-2-(3-chlorophenyl) ethanamine (5.45 g) and 4-{(E)-2-carbomethoxyethenyl}phenylpropan-2-one (7.11 g). The resulting oil was chromatographed on Kieselgel 60. Elution with 5% methanol-chloroform gave the title compound, 9.8 g $\tau$ ($CDCl_3$) 8.9 (3H, d, J=6 Hz), 6.8–7.5 (7H, m, 2H disappears with $D_2O$), 6.25 (3H, s), 5.4 (1H, m), 3.6 (1H, d, J=16 Hz), 2.5–2.9 (8H, m), 2.35 (1H, d, J=16 Hz).

EXAMPLE 6

N-{2-(4-{2-Carboethoxy-2-methylethenyl}-phenyl)-1-methylethyl}-2-hydroxy-2-phenylethanamine This was prepared in an identical manner to the compound described in Example 1 using 2-hydroxy-2-phenylethanamine (0.51 g) and 4-{2-carboethoxy-2-methylethenyl}phenylpropan-2-one (1.0 g). The title compound was isolated as an oil (1.4 g). The oil was dissolved in methanol and treated with fumaric acid (0.43 g) in methanol. Evaporation of the solvent gave an oil which was triturated with ethyl acetate and recrystallized from ethyl acetate to give the title compound hemifumarate (0.38 g) as a 50:50 mixture of diastereoisomers m.p. 135°–138° C. $\tau$($CDCl_3$) 8.8 (3H, d, J=6 Hz), 8.7 (3H, t, J=7 Hz) 8.0 (3H, s), 6.35–7.5 (7H, m, 2H disappears with $D_2O$), 5.8 (2H, q, J=7 Hz) 4.85 (1H, m), 3.15 (1H, s), 2.8 (9H, m), 2.47 (1H, s), 1.8 (2H, broad, disappears with $D_2O$).

EXAMPLE 7

N-{2-(4-{(E)-2-Carboxyethenyl}phenyl)-1-methylethyl}-2-hydroxy-2-phenyl ethanamine, sodium salt.

Sodium hydroxide (0.31 g) in water (10 ml) was added to N-{2-(4-{(E)-2-carbomethoxyethenyl}-1-methylethyl}-2-hydroxy-2-phenylethanamine (2.6 g) in methanol (20 ml) and the solution refluxed for 3 h. The solvent was evaporated and the resulting solid recrystallised from ethanold to give the title compound (0.6 g) containing 0.5 mole of sodium hydroxide m.p. >270° C. $\pi$ ($DMSOd_6+MeOHd_4$) 9.1 (3H d, J=6 Hz), 7.0–7.5 (5H, m), 5.4 (1H, m), 3.6 (1H, d, J=16 Hz), 2.5–3.0 (10H, m).

EXAMPLE 8

N-{2-(4-{(E)-2-Carbomethoxyethenyl}phenyl)-1-methylethyl}-2-hydroxy-2-(3-trifluoromethylphenyl)ethanamine This was prepared in an identical manner to the compound described in Example 1 using 2-hydroxy-2-(3-trifluoromethylphenyl)ethanamine (2.05 g) and 4-{(E)-2-carbomethoxyethyl}phenyl propan-2-one (2.18 g). Elution with 2% methanol chloroform on Kieselgel 60 gave the title compound 1.48 g (hexane), m.p. 80°-83° C. as a 45:55 mixture of diastereoisomers. τ(CDCl₃) 8.95 (3H, d, J=6 Hz), 6.9-7.7 (7H, m, 2H disappears on D₂O), 6.25 (3H, s), 5.4 (1H, m), 3.6 (1H, d, J=16 Hz), 2.5-2.9 (8H, m), 2.45 (1H, d, J=16 Hz).

EXAMPLE 9

N-{3-(4-{(E)-2-Carbomethoxyethenyl}phenyl)-1-methylpropyl}-2-hydroxy-2-(3-chlorophenyl) ethanamine This was prepared in an identical manner to the compound described in Example 1 using 2-hydroxy-2-(3-chlorophenyl) ethanamine (1.71 g) and 4-{(E)-2-carbomethoxyethenyl}phenylbutan-2-one (2.32 g). Elution with 1% methanolchloroform on Kieselgel 60 gave the title compound (0.86 g), m.p. 87°-89° C. (hexane) as a 50:50 mixture of diastereoisomers. τ(CDCl₃), 8.9 (3H, d, J=6 Hz), 8.15-8.55 (2H, m), 6.9-7.7 (7H, m, 2H disappears with D₂O), 6.3 (3H, s), 5.45 (1H, m), 3.65 (1H, d, J=16 Hz), 2.55-2.9 (8H, m), 2.4 (1H, d, J=16 Hz).

EXAMPLE 10

N-{2-(4-{(E)-2-Carbomethoxyethenyl}phenyl)-1-methylethyl}-2-hydroxy-2-(2-fluorophenyl) ethanamine This was prepared in an identical manner to the compound described in Example 1 using 2-hydroxy-2-(2-fluorophenyl) ethanamine (1.55 g) and 4-{(E)-2-carbomethoxyethenyl}phenylpropan-2-one (2.18 g). Elution with 1% methanolchloroform on Kieselgel 60 gave the title compound (1.2 g) m.p. 111°-116° C. (benzene-heptane) as an ~40:60 mixture of diastereoisomers. τ(CDCl₃) 8.95 (3H, d, J=6 Hz), 6.85-7.7 (7H, m, 2H disappears with D₂O), 6.25 (3H, s), 5.1 (1H, m), 3.6 (1H, d, J=16 Hz), 2.5-3.2 (8H, m), 2.35 (1H, d, J=16 Hz).

EXAMPLE 11

N-{2-(4-{(E)-2-Carbomethoxyethenyl}phenyl)-1-methylethyl}-2-hydroxy-2-(3-fluorophenyl) ethanamine This was prepared in an identical manner to the compound described in Example 1 using 2-hydroxy-2-(3-fluorophenyl) ethanamine (1.55 g) and 4{(E)-2-carbomethoxyethenyl}phenylpropan-2-one (2.18 g). Elution with 1% methanolchloroform on Kieselgel 60 gave the title compound (1.4 g) m.p. 75°-110° C. (benzene-heptane) as an ~45:55 mixture of diastereoisomers. τ(CDCl₃) 8.9 (3H, d, J=6 Hz), 6.9-7.8 (7H, m, 2H disappears with D₂O), 6.25 (3H, s), 5.45 (1H, m), 3.6 (1H, d, J=16 Hz), 2.55-3.2 (8H, m), 2.35 (1H, d, J=16 Hz).

EXAMPLE 12

N-{2-(4-{(E)-2-Carbomethoxyethenyl}-phenyl)-1-methylethyl}-2-hydroxy-2-(3-bromophenyl)ethanamine This was prepared in an identical manner to the compound described in Example 1 using 2-hydroxy-2-(3-bromophenyl) ethanamine (2.16 g) and 4-{(E)-2-carbomethoxyethenyl}phenylpropan-2-one (2.18 g). Elution with 1% methanolchloroform on Kieselgel 60 gave the title compound as a solid 1.6 g (benzene-petrol 80-100) m.p. 105°-111° C. as a 42:58 mixture of diastereoisomers. τ(CDCl₃) 8.95 (3H, d, J=6 Hz), 6.9-7.7 (7H, m, 2H disappears with D₂O), 6.2 (3H, s), 5.5 (1H, m), 3.6 (aH, d, J=16 Hz) 2.55 (8H, m), 2.35 (1H, d, J=16 Hz).

EXAMPLE 13

N-{2-(4-{2-Carbomethoxy-1-methylethenyl}phenyl)-1-methylethyl}-2-hydroxy-2-phenylethanamine A mixture of phenylglyoxal monohydrate (0.86 g) and 2-{4-(2-carbomethoxy-1-methylethenyl)phenyl}-1-methylethanamine (1.4 g) was refluxed in benzene (100 ml) under a Dean and Start head until removal of water was complete (4 h).

The solvent was evaporated, methanol (50 ml) added followed by sodium borohydride (0.5 g) and the solution left for 10 min. The methanol was evaporated, the residue shaken with water and extracted with ethyl acetate. The organic layers were combined, dried (MgSO₄) and evaporated to give an oil which was chromatographed on Kieselgel 60. Elution with 2% methanol-chloroform gave the title compound as a mixture of diastereoisomers m.p. 75°-85° C. (hexane). τ(CDCl₃) 8.94 (3H, d, J=6 Hz), 7.45 (3H, d, J=1.5 Hz) 6.9-7.6 (5H, m), 6.25 (3H, s), 4.3 (1H, m), 3.87 (1H, q, J=1.5 Hz), 2.5-3.0 (9H, m).

EXAMPLE 14

N-{3-(4-{2-Carbomethoxy-1-methylethenyl}phenyl)-1,1-dimethylpropyl}-2-hydroxy-2-phenylethanamine This was prepared in an identical manner to the compound described in Example 13 using phenylglyoxal monohydrate (1.34 g) and 3-{4-(2-carbomethoxy-1-methylethenyl)phenyl}-1, 1-dimethylpropanamine (2.61 g). The title compound (2.17 g) m.p. 98°-102° C. (benzene-hexane) was obtained after chromatography on Kieselgel 60 eluting with 1% methanolchloroform. τ(CDCl₃) 8.85 (6H, s), 8.1-8.7 (2H, m), 6.8-7.8 (9H, m), 6.2 (3H, s), 5.3 (1H, dd), 3.82 (1H broad), 2.65 (9H, m).

EXAMPLE 15

N-{2-(4-{2-Carbomethoxy-1-methylethenyl}phenyl)ethyl}-2-hydroxy-2-phenylethanamine This was prepared in an identical manner to the compound described in Example 13 using phenylglyoxal monohydrate (1.50 g) and 2-{4-(2-carbomethoxy-1-methylethenyl) phenyl} ethanamine (2.19 g). The title compound (1.18 g) m.p. 120°-125° C. (benzene-hexane) was obtained after chromatography on Kieselgel 60 eluting with 1% methanol-chloroform. τ (CDCl₃) 7.5 (3H, d, J=1.5 Hz), 7.5 (2H, m), 7.2 (6H, m), 6.3 (3H, s), 5.29 (1H, dd), 3.87 (1H, q, J=1.5 Hz), 2.85 (2H, d, J=9 Hz), 2.7 (5H, s), 2.6 (2H, d, J=9 Hz).

EXAMPLE 16

N-{2-(4-{2-Carbomethoxy-1-methylethenyl}phenyl)-1,1-dimethylethyl}-2-hydroxy-2-phenylethanamine This was prepared in an identical manner to the compound described in Example 13 using phenylglyoxal monohydrate (1.5 g) and 2{4-(2-carbomethoxy-1-methylethenyl)phenyl}-1, 1-dimethylethanamine (2.47 g). The title compound (2.02 g) m.p. 98°-103° C. (benzene/hexane) was obtained after chromatography on Kieselgel 60 eluting with 1% methanolchloroform. τ(CDCl₃) 8.9 (6H, s), 7.55 (3H, d, J=1.5 Hz), 7.35 (2H, s), 6.8-7.6 (4H, m) 6.3 (3H, s), 5.4 (1H, dd) 3.85 (1H, q, J=1.5 Hz), 3.0-2.2 (9H, m).

EXAMPLE 17

N-{2-(4-{2-Carbomethoxy-1-methylethenyl}-phenyl)-1-(R)-1-methylethyl}-2-hydroxy-2-(3-trifluoromethylphenyl) ethanamine This was prepared as a 39:61 mixture of diasterooisoners in an identical manner to the compound described in Example 13 using 3-trifluoromethylphenylglyoxal (1.06 g) and 2{4-(2-carbomethoxy-1-methylethenyl) phenyl}-1-(R)-1-methylethanamine (1.3 g). γ(CDCl$_3$) 8.9 (3H, d, J=6 Hz), 7.4 (3H, s), 6.8–7.6 (7H, m), 6.29 (3H, s), 5.3 (1H, m), 3.9 (1H, bs), 2.3–3.05 (8H, m).

EXAMPLE 18

Separation of the diastereoisomers of the compound of Example 5

N-{2-(4-{(E)-2-Carbomethoxyethenyl}-phenyl)-1-methylethyl}-2-hydroxy-2-(3-chlorophenyl)ethanamine (9.8 g) was recrystallized from methanol to give 2.06 g, m.p. 106°–20° C. of 35:65 diastereoisomer ratio. This sample was re-crystallized again from methanol to give 1.0 g, m.p. 120°–123° C. of <5:>95 diastereoisomer ratio (RS,SR). $^{13}$Cnmr (DMSO d$_6$) 20.06 ppm.

The original mother liquor was evaporated and the resulting solid recrystallised from methanol to provide a 0.71 g sample, m.p. 96°–100° C. consisting of a 63:37 mixture of diastereoisomers. A second crop (1.52 g), m.p. 101–106° C. was obtained by concentration of this mother liquor consisting of an 80:20 mixture of diastereoisomers. $^{13}$Cnmr (DMSO d$_6$) 19.77 and 20.02 ppm.

EXAMPLE 19

Separation of the diastereoisomers of the compound of Example 8

N-{2-(4-{(E)-2-Carbomethoxyethenyl}phenyl)-1-methylethyl}-2-hydroxy-2-(3-trifluoromethylphenyl)ethanamine (5.4 g) was recrystallized from benzene to give 0.25 g, M.P. 97°–105° C. A second crop (0.66 g), m.p. 95°–105° C. was obtained after concentration of the mother liquor. These two crops were combined and recrystallized from hexane to give 0.61 g m.p. 105°–108° C. of 15:85 diastereoisomer ratio. A further recrystallization from benzene-hexane gave 0.33 g, m.p. 107°–109° C. of 3:97 diastereoisomer ratio (RS,SR) 13$_C$ nmr (DMSOd$_6$) 20.16 ppm.

Hexane was added to the original mother liquor to give a further crop 1.22 m.p. 95°–102° C. of 38:62 diastereoisomer ratio. The filtrate ws evaporated and the residue (2.0 g) recrystallized twice from benzene-hexane to give 0.6 g m.p. 89–91 of 90:10 diastereoisomer ratio. $^{13}$Cnmr (DMSOd$_6$) 19.94 ppm and 20.16 ppm.

DESCRIPTION 1

4-{(E)-2-Carbomethoxyethenyl}phenylpropan-2-one

Concentrated hydrochloric acid (309 ml) was added dropwise to a suspension of 1-(4-{(E)-2-carbomethoxyethenyl}-2-nitroprop-1-ene (49.4 g) and iron powder (49.4 g) in methanol (500 ml) at reflux. The solution was refluxed for 1 h at the end of the addition. Water (500 ml) was added, the methanol evaporated and the aqueous extracted with chloroform (3×300 ml). The combined chloroform layers were washed with water, sodium bicarbonate solution and dried (MgSO$_4$). Removal of the solvent gave the title compound (40.3 g). ~(CDCl$_3$) 7.85 (3H, s), 6.3 (2H, s), 6.2 (3H, s), 3.6 (1H, d, J=16 Hz), 2.75 (2H, d, J=8 Hz), 2.5 (2H, d, J=8 Hz), 2.32 (1H, d, J=16 Hz).

DESCRIPTION 2

1-(4-{(E)-2-carbomethoxyethenyl}phenyl)-2-nitroprop-1-ene

A mixture of n-butylamine (36.5 ml) and 4-{(E)-2-carbomethoxyethenyl}benzaldehyde (50.7 g) was refluxed in benzene under Dean and Stark conditions for 2 h. The solvent was removed under reduced pressure, replaced with glacial acetic acid and nitroethane (49 ml) added. The solution was heated to 110° C. and kept at this temperature for 0.75 h. On cooling the title compound (49.5 g) precipitated. (CDCl$_3$) 7.6 (3H, s), 6.2 (3H, s), 3.3 (1H, d, J=16 Hz), 2.0–2.5 (5H, m) 1.9 (1H, s).

DESCRIPTION 3

4-{2-Carboethoxy-2-methylethenyl}phenylpropan-2-one

A mixture of 4-formylphenylpropan-2-one-2-ethylene acetal (3.11 g) and 1-carboethoxyethylidenetriphenylphosphorane (5.47 g) was refluxed in tetrahydrofuran under nitrogen for 1 h. The solvent was evaporated and the residue chromatographed on alumina (200 g). Elution with dichloromethane gave the title compound as the ethylene acetal (1.7 g). This was dissolved in ethanol-2 N hydrochloric acid and stirred at ambient temperature until tlc showed no acetal present. The aqueous was extracted with ether (3×50 ml) and the combined ether layers washed with water (×2), sodium bicarbonate solution, and dried (MgSO$_4$). Removal of the solvent gave the title compound (1.05 g). τ(CDCl$_3$) 8.7 (3H, t, 3=7 Hz), 7.92 (3H, s), 7.9 (3H, s), 6.35 (2H, s), 5.8 (2H, q, J=7 Hz), 2.8 (2H, d, J=8 Hz), 2.6 (2H, d, J=8 Hz), 2.35 (1H, broad s).

DESCRIPTION 4

4-Formylphenylpropan-2-one-2-ethylene acetal

A mixture of 4-hydroxymethylphenylpropan-2-one, ethylene acetal (5.0 g) and manganese dioxide (45 g) was stirred in chloroform at ambient temperature for 2 days. Filtration and removal of the solvent gave the title compound (4.83 g). τ(CDCl$_3$) 8.7 (3H, s), 7.05 (2H, s), 6.05–6.45 (4H, m), 2.6 (2H, d, J=8 Hz), 2.3 (2H, d, J=8 Hz), 0.1 (1H, s).

DESCRIPTION 5

4-{(E)-2-Carbomethoxyethenyl}phenylbutan-2-one

A mixture of 4-{(E)-2-carbomethoxyethenyl}toluene (17.6 g), N-bromosuccinimide (17.8 g) and a trace of dibenzoxylperoxide was refluxed in carbon tetrachloride under illumination until the brown-red colour disappeared. Filtration and evaporation of the solvent gave 4-{(E)-2-carbomethoxyethenyl}benzyl bromide (25.3 g). This was dissolved in dry tetrahydrofuran, heated with the sodium salt of ethyl acetoacetate (15.2 g) and a trace of potassium iodide and refluxed for 1.5 days. The solvent was removed the residue partitioned between ether and water and the ether layer dried. Removal of the solvent gave an oil (26.6 g). This was stirred with sodium hydroxide (10 g) in water (400 ml) for 2 days. The solution was extracted with ether, the aqueous layer made acidic with hydrochloric acid and this was heated on a steam bath for 1 h. The solution was extracted with chloroform and the organic layer dried (MgSO$_4$). Removal of the solvent gave the acid of the title compound (11.0 g). This was esterified with methanol-sulphuric acid to give the title compound. $\tau$(CDCl$_3$) 7.9 (3H, s), 7.0–7.5 (4H, m), 6.25 (3H, s), 3.65 (1H, d, J=16 Hz), 2.85 (2H, d, J=8 Hz), 2.6 (2H, d, J=8 Hz), 2.4 (1H, d, J=16 Hz).

DESCRIPTION 6

2-{4-(2-Carbomethoxy-1-methylethenyl)phenyl}-1-methylethanamine

A solution of sodium hydroxide (6 g) in water (30 ml) was added to N-acetyl-2-{4-(2-carboethoxy-1-methylethenyl)phenyl}-1-methylethanamine (8.5 g) and the mixture stirred and heated under reflux for 8 hrs. The solution was cooled and evaporated to dryness. The residue was dissolved in methanol (30 ml) and made acid by addition of conc. HCl. The precipitated sodium chloride was removed by filtration, and the methanol solution dried over molecular sieves overnight. This solution was then added to a solution of thionyl chloride (8 ml) in dry methanol (10 ml) kept at −70° C. by Dry Ice/acetone. After warming to ambient temperature, the solution was stirred and heated under reflux for 1 hour. The solution was cooled, filtered and evaporated, the residue shaken with an aqueous solution of potassium carbonate and extracted with chloroform. The chloroform extract was dried (MgSO$_4$) and evaporated to leave an oil, (2.8 g). $\tau$(CDCl$_3$) 8.9 (3H, d, J=8 Hz), 8.5 (2H, bs, exchangeable with D$_2$O), 7.45 (3H, d, J=1.5 Hz). 7.2–7.4 (2H, m), 6.6–7.0 (1H, m), 6.3 (3H, s), 3.92 (1H, q, J=1.5 Hz), 2.5–3.0 (4H, m).

DESCRIPTION 7

N-Acetyl-2-{4-(2-carboethoxy-1-methylethenyl)phenyl}-1-methylethanamine

To a solution of triethylphosphonoacetate (10.81 g) in dry THF under nitrogen, was added sodium hydride (1.17 g) and the mixture stirred for 0.5 hours. A solution of N-acetyl-2-(4-acetylphenyl)-1-methylethanamine (10.57 g) in THF was then added and the mixture heated under reflux until reaction was complete (followed by t.l.c). After cooling to ambient temperature, the solution was filtered through celite and the THF evaporated. The residue was dissolved in ethyl acetate and chromatographed on silica gel, eluting with ethyl acetate to give the title compound (8.5 g) ~(CDCl$_3$) 8.9 (3H, d, J=7 Hz), 8.7 (3H, t, J=7 Hz), 8.1 (3H, s), 7.48 (3H, s), 7.15–7.35 (2H, m), 6.0 (1H, m), 5.83 (2H, q, J=7 Hz), 4.6 (1H, b) 3.9, 4.15 (1H, s, s) 2.5–3.0 (4H, m).

DESCRIPTION 8

3-{4-(2-Carbomethoxy-1-methylethenyl)phenyl}-1,1-dimethylpropanamine

This was prepared in an identical manner to the compound described in Description 6 using N-formyl-3-{4-(2-carboethoxy-1-methylethenyl)phenyl}-1, 1-dimethylpropanamine. $\tau$(CDCl$_3$/D$_2$O(8.8 (6H, s) 8.5–8.1 (2H, m), 7.48 (3H, d, J=1.5 Hz), 7.5–7.1 (2H, m), 6.3 (3H, s), {4.1 (broad) +3.88 (q, J=1.5 Hz), Total 1H}, 2.8 (2H, d, J=7 Hz), 2.55 (2H, d, J=7 Hz).

DESCRIPTION 9

N-Formyl-3-{4-(2-carboethoxy-1-methylethenyl)phenyl}-1, 1-dimethylpropanamine

This was prepared in an identical manner to the compound described in Description 7 using N-formyl-3-(4-acetylphenyl) -1, 1-dimethylpropanamine (17.25 g), triethylphosphonoacetate (16.6 g) and sodium hydride (1.78 g) and gave the title compound (12.7 g). $\tau$(CDCl$_3$) 8.65 (3H, t, J=6 Hz), 8.6 (6H, s), 8.4–7.9 (2H, m), 7.45 (3H, d, J=1.5 Hz), 7.5–7.0 (2H, m), 5.8 (2H, q, J=6 Hz), {4.2 (broad) +3.9 (q, J=1.5 Hz), Total 1H}, 3.4 (1H, borad), 2.6 (4H, m), 2.1 (1H, d, J=5 Hz).

DESCRIPTION 10

N-Formyl-3-(4-acetylphenyl)-1,1-dimethylpropanamine

N-Formyl-3-phenyl-1, 1-dimethylpropanamine (115 g) was dissolved in 1,2-dichloroethane (850 ml) at 0° C. Acetyl bromide (116 ml) was added followed by the portionwise addition of aluminum chloride (263 g) over 0.5 h. At the end of addition the mixture was allowed to warm to room temperature and then refluxed for 1h. The hot solution was poured onto crushed ice (3 Kg) and the mixture extracted with chloroform. The chloroform extracts were washed with water, sodium bicarbonate and dried (MgSO$_4$). Evaporation of the solvent gave an oil of which 25 g was chromatographed on Kieselgel 60 (1 Kg). Elution with 1% methanol-chloroform gave the title compound as an oil (18 g). $\tau$(CDCl$_3$) 8.6 (6H, s) 8.4–7.75 (2H, m), 7.45 (3H, s), 7.5–7.05 (2H, m), 3.0–4.0 (1H, broad), 2.7 (2H, d, J=8 Hz), 2.15 (2H, d, J=8 Hz) 1.2 (1H, d, J=5 Hz).

DESCRIPTION 11

2-{4-(2-Carbomethoxy-1-methylethenyl)phenyl}ethanamine

This was prepared in an identical manner to the compound described in Description 6 using N-formyl-2-{4-(2-carboethoxy-1-methylethenyl)phenyl}ethanamine. $\tau$(CDCl$_3$) 8.2 (2H, broad), 7.35 (3H, d, J=1.5 Hz), 7.3–6.7 (4H, m), 6.2 (3H, s), 3.8 (1H, broad), 2.8 (2H, d, J=8 Hz), 2.5 (2H, d, J=8 Hz).

DESCRIPTION 12

N-Formyl-2-{4-(2-Carboethoxy-1-methylethenyl)phenyl}ethanamine

This was prepared in an identical manner to the compound described in Description 7 using N-formyl-2-(4-acetyl phenyl)ethanamine (17.6 g), triethylphosphonoacetate (20.6 g) and sodium hydride (2.2 g) and gave the title compound (13.2 g). $\tau$(CDCl$_3$), 8.7 (3H, t, J=7 Hz), 7.5+7.45 (3H, s+s), 7.2 (2H, t, J=7 Hz), 6.45 (2H, m), 5.75 (2H, q, J=7 Hz), 4.1+3.85 (1H, s+s), 4.1 (1H, broad) 2.8 (2H, d, J=8Hz), 2.55 (2H, d, J=8 Hz), 1.85 (1H, broad).

DESCRIPTION 13

N-Formyl-2-(4-acetylphenyl) ethanamine

This was prepared in an identical manner to the compound described in Description 10 using N-formyl-2-phenylethanamine (95 g), acetylbromide (128 ml), aluminium chloride (288 g) in 1,2-dichloroethane (900 ml). 25 g of the crude produce was chromatographed on Kieselgel 60 (1 Kg). Elution with 1% methanol-chloroform gave the title compound as an oil (18 g). $\tau$(CDCl$_3$) 7.42 (3H, s), 7.1 (2H, t, J=7 Hz), 6.5 (2H, m), 3.45 (1H, broad), 2.7 (2H, d, J=8 Hz) 2.1 (2H, d, J=8 Hz), 1.9 (1H, s).

DESCRIPTION 14

2-{4-(2-Carbomethoxy-1-methylethenyl)phenyl}-1,1-dimethylethanamine

This was prepared in an identical manner to the compound described in Description 6 using N-formyl-2-{4-(2-carboethoxy-1-methylethenyl)phenyl}-1,1-dimethylethanamine $\tau(CDCl_3)$ 8.8 (6H, s), 8.55 (2H, broad), {7.75 (d) =7.3 (d J=1.5 Hz), Total 3H}, 7.25 (2H, s), 6.15 (3H, s), {4.0+3.75 (q, J=1.5 Hz), Total 1H}, 2.75 (2H, d, J=8 Hz), 2.5 (2H, d, J=8 Hz).

DESCRIPTION 15

N-Formyl-2-{4-(2-Carboethoxy-1-methylethenyl)-phenyl}-1,1-dimethyl ethanamine

This was prepared in an identical manner to the compound described in Description 7 using N-formyl-2-{4-acetylphenyl}-1,1-dimethylethanamine (11.4 g), triethylphosphonoacetate (11.7 g), and sodium hydride (1.25 g) and gave the title compound (10.2 g). $\tau(CDCl_3)$ 8.7 (3H, t, J=7 Hz), 8.69 (6H, s), {7.85 (s) +7.45 d, J=1.5 Hz, Total 3H}, 7.2+6.9 (2H, s+s), 5.75 (2H, q, J=7 Hz), 4.7 (1H, broad), {4.1 (s) +3.85 (broad) 1H}, 2.6 (4H, m), 1.9 (1H, s).

DESCRIPTION 16

N-Formyl-2-(4-acetylphenyl)-1,1-dimethylethanamine

This was prepared in an identical manner to the compound described in Description 10 using aluminum chloride (26 g), acetyl bromide (115 ml) and N-formyl-2-phenyl-1, 1-dimethylethanamine (101.5 g) in 1,2-dichloroethane, (850 ml). $\tau(CDCl_3)$. 8.62 (6H, s), 7.45 (3H, s), 7.1+6.85 (2H, s+s), 3.85 (1H, broad) 2.7 (2H, d, J=8 Hz) 2.1 (2H, d, J=8 Hz), 1.9 (1H, s).

DESCRIPTION 17

2-{4-(2-Carbomethoxy-1-methylethenyl)phenyl}-1-(R)-1-methylethanamine

This was prepared in an identical manner to the compound described in Description 6 using N-acetyl-2-{4-(2-carboethoxy-1-methylethenyl)phenyl}-1-(R)-1-methylethanamine (7 g). The title compound (1.3 g) was isolated as an oil. $\tau(CDCl_3)$ 8.88 (3H, d, J=6 Hz), 8.5 (2H, bs replaceable with $D_2O$), 7.8+7.4 (3H, d), 7.3 (2H, m), 6.5-7.1 (1H, m), 6.2 (3H, s), 3.9+4.5 (1H, q), 2.5 -2.95 (4H, m).

DESCRIPTION 18

N-Acetyl-2-{4-(2-carboethoxy-1-methylethenyl)-phenyl}-1-(R)-methylethanamine

This was prepared in an identical manner to the compound described in Description 7 using N-acetyl-2-(4-acetylphenyl)-1-(R)-1-methylethanamine (10.57 g) ({$\alpha_D^{20}$+20.28 (MeOH), sodium hydride (1.3 g) and triethylphosphonoacetate (10.81 g) in dry THF. The title compound was isolated as an oil (7 g) after chromatography on Kieselgel 60 eluting with 1% methanol-chloroform. $\tau(CDCl_3)$ 8.85 (3H, d, J=6 Hz), 8.65 (3H, t, J=75 Hz), 8.05 (3H, s), 7.8+7.40 (3H, d, J=1.5 Hz). 7.20 (2H, m) 5.8 (2H, q, J=7 Hz), (1H, m), 4.0 (1H, b, d), 4.15+3.85 (1H, q), 2.5-2.95 (4H, m).

DEMONSTRATION OF EFFECTIVENESS OF COMPOUNDS

(i) Anti-obesity activity

The compounds were dosed daily in water or carboxymethyl-cellulose suspension to genetically obese mice by oral gavage for 28 days. At the end of the time the carcass composition was determined. The results obtained were as follows:

| COMPOUND OF EXAMPLE | DOSE mg/kg p.o | g-LIPID PER MOUSE TREATED | g-LIPID PER MOUSE CONTROL |
|---|---|---|---|
| 1 | 25 | 14.8 | 19.5 |
| 3 | 10.5 | 14.2 | 19.1 |
| 4 | 10.5 | 15.7 | 17.9 |
| 5(18)(m.p.101–6° C.) | 10.4 | 14.3 | 19.2 |
| 5(18)(m.p.120–3° C.) | 10.4 | 15.1 | 19.2 |
| 6 | 12.0 | 17.3 | 20.2 |
| 7 | 10.0 | 18.3 | 20.2 |
| 8 | 11.3 | 16.3 | 21.3 |

(ii) Effect on energy expenditure

The effect of the compounds on the energy expenditure of mice was demonstrated by means of the following procedure.

Female CFLP mice each weighing approximately 24 g, were given as much food and water as they wanted before and during the experiment. The compounds were dissolved in water by addition of the same number of moles hydrochloric acid, and these solutions were dosed orally to each of 12 mice. A further 12 mice were dosed orally with water. The mice were placed in boxes through which air was drawn and the oxygen content of the air leaving the boxes was measured. The energy expenditure of the mice was calculated for 21 hours after dosing from the volume of air leaving the boxes and its oxygen content following the principles described by J. B. de V. Weir (J. Physiol. (London) (1949) 109, 1–9). The food intake of the mice was measured over this same period of 21 hours. The results are expressed as a percentage of the mean food intake or rate of energy expenditure of the mice dosed with water.

| COMPOUND OF EXAMPLE | DOSE mg/kg p.o | PERCENTAGE OF CONTROL VALUES ENERGY EXPENDITURE | PERCENTAGE OF CONTROL VALUES FOOD INTAKE |
|---|---|---|---|
| 1 | 25 | 130 | 98 |
| 2 | 20 | 121 | 92 |
| 3 | 21 | 119 | 96 |
| 4 | 21 | 111 | 98 |
| 5(18)(m.p.101–6° C.) | 4.3 | 121 | 90 |
| 5(18)(m.p.120–3° C.) | 4.3 | 111 | 88 |
| 6 | 24 | 126 | 98 |
| 7 | 20.5 | 121 | 102 |
| 8(19)(m.p.107–109° C.) | 22.7 | 107 | 78 |
| 8(19)(m.p.89–91° C.) | 22.7 | 147 | 69 |
| 9 | 21.5 | 111 | 97 |
| 10 | 20 | 122 | 119 |
| 11 | 20 | 119 | 106 |
| 12 | 23 | 138 | 103 |
| 13 | 20.5 | 120 | 106 |
| 14 | 21 | 106 | 97 |
| 15 | 19 | 105 | 83 |
| 16 | 20 | 130 | 92 |
| 17 | 23.5 | 148 | 104 |

(iii) Cardiac Activity

Rat hearts were perfused by the Langendorff procedure. Hearts were dissected free within 30 seconds of death and reverse perfused via the aorta and coronary vessels with Krebs-Ringer bicarbonate solution (ph 7.4, 37° C.) gassed with 95% $O_2$:5% $CO_2$. The flow rate was between 8–12 mls/minute. Responses were obtained after injection of drug dissolved in isotonic saline into the perfusion media. Heart rate and tension were displayed on an Ormed MX2P recorder via a tension tranducer and heart ratemeter.

Results are expressed as a percentage of the response due to salbutamol.

| COMPOUND OF EXAMPLE | DOSE ADDED (ug) | HEART TENSION | HEART RATE |
|---|---|---|---|
| 1 | 30 | 12 | 0 |
| 2 | 30 | 55 | 120 |
| 3 | 30 | 55 | 80 |
| 4 | 30 | 8 | 13 |
| 5(18)(m.p.101–6° C.) | 30 | 4 | 10 |
| 5(18)(m.p.120–3° C.) | 30 | 17 | 0 |
| 6 | 10 | 28 | 15 |
| 7 | 30 | 60 | 40 |
| 8 | 30 | 6 | 0 |
| 9 | 30 | 14 | 6 |
| 10 | 30 | 33 | 8 |
| 11 | 10 | 12 | 43 |
| 12 | 30 | 0 | 0 |
| 13 | 30 | 50 | 54 |
| 14 | 30 | 6 | 0 |
| 15 | 30 | 0 | 0 |
| 16 | 30 | 27 | 0 |
| 17 | 30 | 0 | 0 |
| 19(m.p.107–109° C.) | 30 | 0 | 0 |
| 19(m.p.89–91° C.) | 30 | 36 | 62 |

(iv) Hypoglycaemic activity

Female CFLP mice, weighing approximately 25 g, were fasted for 24 hours prior to the study. The compounds under study were dosed orally to each of 8 mice. 30 minutes later a blood sample (20 ml) was obtained from the tail for the analysis of blood glucose. Immediately after taking this blood sample, each mouse was given a glucose load (1 g/kg body weight subcutaneously). Blood samples were then obtained from each mouse at 30 minute intervals for 120 minutes.

Compounds that produced a significant (P<0.05) reduction of blood glucose, compared with control mice given water, at any time interval were considered active. The area under the blood glucose curve over the 2 hour period after giving the glucose load was calculated for each compound and compared with the value for contol animals.

| COMPOUND OF EXAMPLE | DOSE mg/kg p.o. | REDUCTION IN AREA UNDER BLOOD GLUCOSE CURVE % |
|---|---|---|
| 3 | 1 | 36.6 |
| 6 | 1 | 19.9 |
| 8 | 1 | 23.8 |
| 9 | 1 | 17.2 |
| 13 | 1 | 29.2 |
| 14 | 20 | 17.5 |
| 15 | 20 | 48.0 |
| 19(mp 89–91° C.) | 1 | 30.4 |

We claim:
1. A compound of the formula:

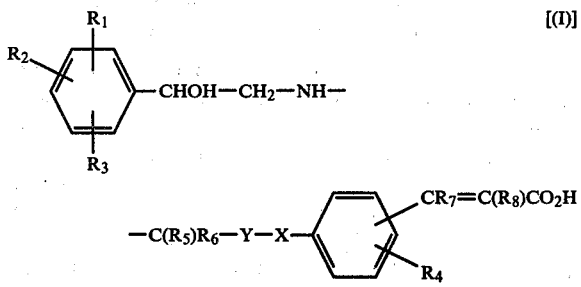

[(I)]

or a pharmaceutically acceptable ester, amide, or salt thereof wherein $R_1$ is hydrogen, fluoro, chloro, bromo, hydroxy, hydroxymethyl, methyl, methoxy, amino, formamido, acetamido, methylsulphonylamido, nitro, benzyloxy, methylsulphonylmethyl, ureido, trifluoromethyl or p-methoxybenzylamino;

$R_2$ is hydrogen, fluoro, chloro, bromo, or hydroxy;
$R_3$ is hydrogen, chloro, bromo or hydroxy;
$R_4$ is hydrogen, chloro, fluoro, methyl, methoxy, hydroxy or carboxylic acid or a salt, ester or amide thereof;
$R_5$ is hydrogen or methyl;
$R_6$ is hydrogen or methyl;
$R_7$ is hydrogen, methyl or ethyl;
$R_8$ is hydrogen, methyl or ethyl;
X is oxygen or a carbon-carbon bond, and
Y is alkylene of up to 5 carbon atoms, or a carbon-carbon bond.

2. A compound according to claim 1 which is an amide of the formula:

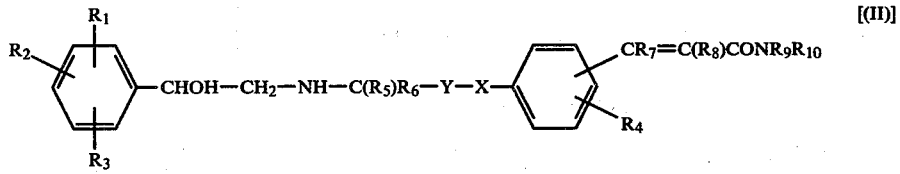

[(II)]

or a pharmaceutically acceptable salt thereof, in which $R_1$, $R_2$, $R_3$, $R_4$, $R_5$, $R_6$, $R_7$, $R_8$, X and Y are as therein defined, and $R_9$ and $R_{10}$ are each alkyl of 1 to 4 carbon atoms or hydrogen.

3. A compound according to claim 1 in which the —$CR_7$= group is para to X.

4. A compound according to claim 1 in which X is a bond.

5. A compound according to claim 1 in which $R_1$ and $R_3$ are hydrogen and $R_2$ is hydrogen, 3-chloro, 4-chloro, 3-trifluoromethyl, 2-fluoro, 3-fluoro, 2-chloro or 3-bromo.

6. A compound according to claim 1 in the form of a single stereoisomer.

7. A compound according to claim 1 in the form of a mixture of stereoisomers.

8. A diastereoisomer of a compound according to claim 1 containing two centres of asymmetry, said diastereoisomer being free of the other diastereoisomer.

9. A compound according to claim 1 and having the formula:

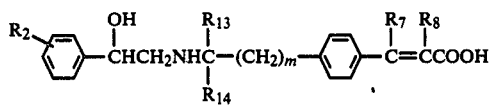

or a pharmaceutically acceptable ester, amide or salt thereof wherein $R_2$ is hydrogen, chloro, fluoro, bromo or trifluoromethyl;

each of $R_7$, $R_8$, $R_{13}$ and $R_{14}$, independently of the other, is hydrogen or methyl; and m is 1, 2 or 3.

10. A compound according to claim 9 wherein $R_2$ is hydrogen, 3-chloro, 3-fluoro, 2-fluoro or 3-trifluoromethyl.

11. A compound according to claim 10 wherein m is 1.

12. A compound according to claim 1 and having the formula:

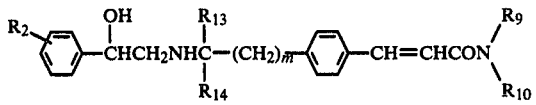

wherein
$R_2$ is hydrogen, chloro, fluoro, bromo or trifluoromethyl;
each of $R_{13}$ and $R_{14}$, independently of the other, is hydrogen or methyl;
each of $R_9$ and $R_{10}$, independently of the other, is hydrogen or alkyl of 1 to 4 carbon atoms; and
m is 1, 2 or 3.

13. A compound according to claim 12 wherein $R_2$ is hydrogen, 3-chloro, 3-fluoro, 2-fluoro or 3-trifluoromethyl.

14. A compound according to claim 13 wherein m is 1.

15. A pharmaceutical composition useful in the treatment of obesity or hyperglycuemia which comprises an effective amount of a compound according to claim 1 and a pharmaceutically acceptable carrier therefor.

16. A composition according to claim 15 in unit dosage form.

17. A composition according to claim 16 in which each unit dose contains from 0.01 to 100 mg of active compound.

* * * * *